United States Patent [19]

Tanihara et al.

[11] Patent Number: 4,472,303
[45] Date of Patent: Sep. 18, 1984

[54] BLOOD PURIFICATION METHOD

[75] Inventors: Masao Tanihara; Toshihide Nakashima, both of Kurashiki; Koichi Takakura, Okayama, all of Japan

[73] Assignee: Kuraray Co., Ltd., Kurashiki, Japan

[21] Appl. No.: 524,931

[22] Filed: Aug. 22, 1983

Related U.S. Application Data

[62] Division of Ser. No. 395,975, Jul. 7, 1982, Pat. No. 4,420,395.

[30] Foreign Application Priority Data

Jul. 10, 1981 [JP] Japan ................................ 56-108670

[51] Int. Cl.³ ...................... B01D 15/08; B01D 39/06; C07G 7/00
[52] U.S. Cl. ................................ 260/112 B; 210/679; 210/691; 210/927
[58] Field of Search ............... 210/679, 690, 691, 692, 210/927, 263, 287, 502.1; 502/407; 260/112 B

[56] References Cited

U.S. PATENT DOCUMENTS

| | | | |
|---|---|---|---|
| 3,637,489 | 1/1972 | Haller | 210/927 |
| 3,661,817 | 5/1972 | Hamilton | 252/428 |
| 3,956,179 | 5/1976 | Sebestian | 252/430 |
| 3,960,521 | 6/1976 | Kruppa | 252/430 |
| 4,029,583 | 6/1977 | Ho Chang | 210/502 |
| 4,118,316 | 10/1978 | Talley | 210/502 |
| 4,140,653 | 2/1979 | Imura | 210/502 |
| 4,171,283 | 10/1979 | Nakashima | 210/502 |
| 4,199,449 | 4/1980 | Slejko | 210/502 |
| 4,202,775 | 5/1980 | Abe | 210/527 |
| 4,246,351 | 1/1981 | Miyake | 260/112 B |
| 4,248,736 | 2/1981 | Fuchigami | 210/502 |
| 4,284,553 | 8/1981 | Brown | 260/112 B |

*Primary Examiner*—Ernest G. Therkorn
*Attorney, Agent, or Firm*—Barry Kramer

[57] ABSTRACT

Treatment of the blood by means of a blood purification device comprising packed, substantially spherical, smooth-surfaced, porous granules having at least 0.1 $\mu$mole/m² of the silanol group on the surface thereof, a blood inlet and a blood outlet scarcely causes decrease in leukocyte or platelet count or blood cell damage and can remove proteins from the blood by adsorption without high pressure loss.

9 Claims, 4 Drawing Figures

BLOOD PURIFICATION METHOD

This application is a division of application Ser. No. 395,975, filed July 7, 1982 now U.S. Pat. No. 4,420,395.

BACKGROUND OF THE INVENTION

1. Field of the Invention

This invention relates to a blood purification device for use in the treatment of immune diseases, cancer diseases, familial hypercholesterolemia, hepatic diseases and renal diseases, among others.

2. Description of the Prior Art

Recently, much attention has been focused on the plasma exchange therapy which can really produce a significant effect in the treatment of immune diseases, cancer diseases, familial hypercholesterolemia, hepatic diseases, renal diseases and so forth, including autoimmune diseases and graft rejection. The effect is supposedly due to the removal of causative substances in the blood, such as antibodies, immunosuppressive factors, low-density lipoprotein (LDL), metabolite-bound proteins, hepatotoxic and nephrotoxic substances, together with the plasma. However, in the plasma exchange therapy, it is necessary to supplement normal human plasma or human serum albumin instead of the discarded patients' plasma and therefore can hardly be applied to the treatment of a large number of patients. The therapy is also wasteful because useful components are also removed together with unnecessary disease-causing substances.

On the other hand, the blood purification method using an adsorbent has an advantage that a supplemental fluid is scarcely needed because unnecessary components alone are removed. However, when activated carbon or a porous resin is used as the adsorbent, low-molecular-weight substances such as creatinine and uric acid can be adsorbed but those causative substances that have a high molecular weight can hardly be removed, so that a satisfactory therapeutic effect cannot be produced. Although some porous resins (e.g. Rohm & Haas' porous resin "Amberlite ® XAD-7") can adsorb proteins having a medium or higher molecular weight, they have a disadvantage that they also adsorb useful components such as vitamins and saccharides or that impurities from the manufacturing process are leached out or minute particles are frequently formed, hence they are less practicable.

As a result of intensive research to overcome these problems, the present inventors previously have found that a porous material having a mean pore diameter of 30–3,000 angstroms with a sharp pore size distribution and preferably having the silanol group on the surface can absorb proteins selectively and have applied for a patent (Ser. No. 250,630). However, it has lately been found that such a porous material as porous glass is generally has a crushed form and each granule thereof has sharp edges, so that, when used in the direct blood treatment, such a material causes decrease in leukocyte or platelet count. Moreover, when crushed granules are packed in a column and the blood or plasma is passed therethrough, the pressure loss within the column increases with the lapse of time in a manner unfavorable to the prolonged blood treatment. As a result of further research in view of the above, it has now been found that the use of porous granules spherical in shape can overcome the above-mentioned disadvantages, and this finding has led to the present invention.

SUMMARY OF THE INVENTION

The invention provides a blood purification device comprising an adsorbent layer of packed, substantially spherical, porous granules having at least 0.1 $\mu$ mole/m$^2$ of the silanol group on the surface thereof, a blood inlet and a blood outlet. It is an object of the invention to provide a blood purification device in which decrease in leukocyte or platelet count, blood cell damage during the blood treatment or pressure loss increase with the lapse of time scarcely occurs. The term "blood" as used herein includes plasma and serum as well as whole blood.

BRIEF DESCRIPTION OF THE DRAWINGS

In the accompanying drawings.

DETAILED DESCRIPTION OF THE INVENTION

The porous granules to be used in the practice of the invention are required to have at least 0.1 $\mu$mole/m$^2$, preferably not less than 0.3 $\mu$mole/m$^2$, more preferably not less than 0.5 $\mu$mole/m$^2$, of the silanol group on the surface thereof. When the silanol content on the surface is less than 0.1 $\mu$ mole/m$^2$, the adsorbent has a low adsorption capacity for proteins and is not suited for the purpose of the present invention. The "silanol" group has the formula $\equiv$Si—OH and the surface concentration thereof is measured by the methyl red absorptiometry. The "surface" includes not only the apparent surface but also the surface within the micropores. As the above-specified porous granules having the silanol group on the surface thereof, there may be mentioned granules of porous glass, porous silica, porous silica-alumina and the like and granules of these and other porous materials with the silanol group introduced therein on the surface thereof by treatment with a sodium silicate solution, coating with a polymer or chemical bonding, for instance.

Figure 1:
FIG. 1 is an electronmicrograph of crushed porous glass granules.
Figure 2:
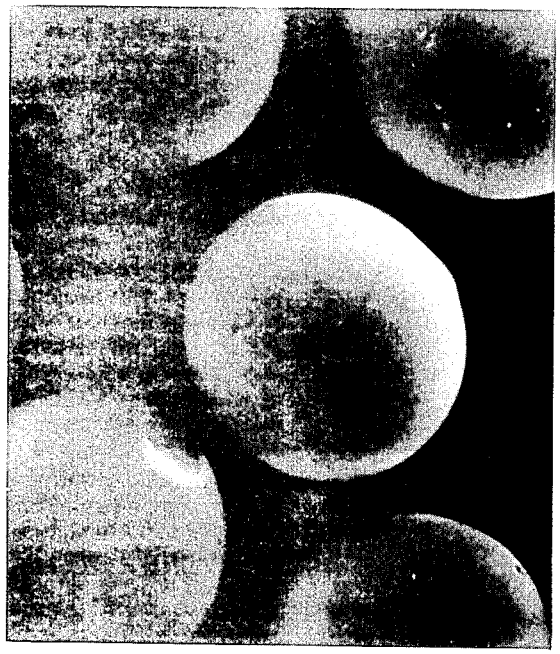
FIG. 2 is an electronmicrograph of spherical porous glass granules.

Porous glass is produced by melting and shaping an alkali borosilicate glass species, heat-treating the shaped glass within the transition temperature region and acid-treating the resulting glass which has undergone fine phase separation. Commercially available porous glass granules are generally produced by crushing a raw material to an appropriate size and consequently have a crushed form as shown in FIG. 1. Spherical porous glass granules can be produced by blowing molten alkali borosilicate glass against a metal plate through a nozzle, heat-treating the shaped material within the transition temperature region and further treating the same with an acid. Said granules may also be produced by treating crushed alkali borosilicate glass granules at a temperature slightly higher than the transition temperature region, further heat-treating the resulting granules, which are now spherical, within the transition temperature range and then treating the same with an acid. An electronmicrograph of spherical porous glass granules is shown in FIG. 2. Porous silica is produced by treating a sodium silicate solution with an acid such as sulfuric acid and drying the resulting hydrogel, if necessary followed by heat treatment. Porous silica-alumina is produced by depositing alumina on silica hydrogel followed by the same treatment as mentioned above. Spherical granules can be produced, for example, by dropping a sodium silicate solution through a nozzle into a two-layer liquid composed of a water-insoluble medium and an aqueous acid solution so as to give a hydrogel with spherical granules dispersed therein. The silanol group introduction by treatment with a sodium silicate solution can be carried out, for example, by immersing porous granules in a sodium silicate solution, collecting the granules by filtration, drying the same, then immersing the same, for instance, in hydrochloric acid, and drying the same under heating. The silanol group introduction by polymer coating can be carried out by coating porous granules with a silanol group-containing polymer (e.g. poly(trimethoxysilylpropyl methacrylate) or an acrylate or methacrylate polymer containing trimethoxysilylpropyl methacrylate as a comonomer). The coating can be performed, for example, by coating porous granules with a solution containing the monomer(s) and, if necessary, a polymerization initiator and then polymerizing the monomer(s) under heating, for instance. The silanol group introduction by chemical bonding can be carried out by directly reacting porous granules with a silane coupling agent.

Among the above-mentioned silanol group-containing porous granules, porous glass granules are preferred in view of high physical strength and high silanol group concentration.

The porous granules to be used in accordance with the invention are required to be substantially spherical. When the granules are not spherical, such as in the case of porous glass granules for general use as produced by crushing a mass of porous glass, they retain edges even after coating treatment and, when in contact with the blood, may unfavorably cause decrease in leukocyte or platelet count or blood cell damage or may promote thrombus formation. Furthermore, when the granules are not spherical, the pressure loss becomes large and therefore such granules are unfavorable for carrying out the blood treatment continuously for many hours. The phrase "substantially spherical" as used herein means that, for each granule, the ratio of the maximum diameter to the minimum diameter is not more than 1.5 and the granule has no sharp edges and is apparently smooth-surfaced or, in other words, has a smooth spherical surface. The adsorbent layer which constitutes the blood purification device in accordance with the invention is formed only with substantially spherical granules.

The porous granules to be used in accordance with the invention preferably have a diameter within the range of 0.1 mm to 5 mm, more preferably within the range of 0.5 mm to 1 mm. When the granule diameter is smaller than 0.1 mm, the pressure loss within the adsorbent layer becomes large and moreover the risk of hemolysis arises. When the granule diameter is greater than 5 mm, increased intergranular spaces unfavorably lower the adsorption efficiency.

Furthermore, the porous granules preferably have a pore volume within the range of 0.3 cc/g to 2.0 cc/g. When the pore volume is less than 0.3 cc/g, the adsorption capacity for proteins is small and the granules are no more suited for the purpose of the invention. When the pore volume is larger than 2.0 cc/g, the skeletal structure becomes fragile and the possibility of minute fragment formation increases. In addition, the porous granules desirably have a pore diameter within the range of 20 angstroms to 3,000 angstroms. When the pore diameter is smaller than 20 angstroms, proteins cannot enter the micropores, hence cannot be adsorbed efficiently. When the pore diameter is greater than 3,000 angstroms, the surface area decreases and the skeletal structure unfavorably becomes fragile.

Furthermore, it is preferable that the pore diameter distribution is uniform because a broad pore diameter distribution results in decreased selectivity in protein adsorption as a function of the protein size. Thus, it is preferable that, when the mean pore diameter is D, the ratio of the volume occupied by pores with diameters within the range of 0.8D to 1.2D to the whole pore volume is at least 80%. When the granules have such a sharp pore diameter distribution, the use of porous granules having an adequate pore diameter depending on the molecular weight of the protein to be adsorbed can result in selective adsorption and removal of the target proteins.

There is a close relationship between the mean pore diameter and the protein species adsorbed. For instance, for adsorption of proteins having a molecular weight of 500 to 20,000, such as immune soluble factors (e.g. cancer cell-derived immunosuppressive factor:IRA (immuno-regulatory $\alpha$-globulin), T-lymphocyte-derived immune soluble factors: TCGF (T cell growth factor), GSF (growth soluble factor), SSF (suppressor soluble factor), TRF (T cell replacing factor) and KHF (killer cell helper factor), thymus-derived soluble factors:LSF (lymphocyte-stimulating factor) and CIF (competence-inducing factor), and macrophage-derived factors:TDF (thymocyte-differentiation factor) and interleukin I), lysozyme, cytochrome C and toxic proteins secreted by venomous snake, scorpion, nocuous sea urchin, venomous spider, frog, wasp, bee and so on, the granules preferably have a mean pore diameter within the range of 20–150 angstroms. Especially for the above-mentioned GSF, the granules preferably have a negatively charged surface, and for SSF, a positively charged surface. The negatively charged surface and the positively charged surface can be obtained by introducing negatively charged groups such as carboxyl or sulfo and positively charged groups such as amino respectively onto the surface. For proteins with a molecular weight of 20,000–200,000, such as $\gamma$-globulin, albumin and immunosuppressive factors, including $\alpha_1$-antitrypsin ($\alpha_1$AT), C-reactive protein (CRP), $\alpha_1$-acid glycoprotein (AAG), immunosuppressive acid protein (IAP) and $\alpha$-fetoprotein (AFP), the granules preferably have a mean pore diameter within the range of 150–1,000 angstroms. $\gamma$-Globulin is a group of proteins with a molecular weight of about 160,000. Among them, immunoglobulin G is the main causative factor in autoimmune diseases. Removal of such causative factor from the blood can contribute to the treatment of the relevant diseases. For adsorption of $\gamma$-globulin, the use of porous granules having a mean pore diameter of 350–900 angstroms (more preferably 400–700 angstroms) is especially preferable since porous granules having a mean pore diameter within the above-mentioned range can adsorb $\gamma$-globulin efficiently and selectively. For LDL having a molecular weight of several millions, the use porous granules having a mean pore diameter within the range of 900–1,600 angstroms is preferable and, for proteins having a molecular weight of 200,000–1,000,000, including immune complexes, fibrinogen, microfibrin and complements, the mean pore diameter is preferably within the range of 1,000–2,500 anstroms.

The porous granules may be packed in a column as they are. For increased compatibility with the blood, however, it is also possible to coat them with a hydrophilic polymer. The method of coating them with a hydrophilic polymer preferably comprises immersing the porous granules in a hydrophilic polymer solution and then removing the solvent. In a more preferable embodiment, a polymer containing a crosslinking agent is used and, after the coating operation, crosslinking is effected by heating. In such a process, the hydrophilic polymer scarcely penetrate into the micropores of the porous granules and accordingly the risk of a drop in performance due to covering of the silanol group on the pore inside surface (wall) is scarce. Examples of the hydrophilic polymer are acrylic acid ester-based polymers, methacrylic acid ester-based polymers, acrylamide-based polymers, vinyl alcohol-based polymers, polyvinylpyrrolidone, cellulose nitrate and gelatin.

The column packed with the porous granules preferably comprises a main body element fitted with a blood inlet and a blood outlet, each of a shape easily connectable with a blood circuit, with the porous granule layer therebetween, and further fitted with 80–180 mesh filters, which allow passage of the blood but not of the porous granules, on either side of the adsorbent layer (i.e. between the layer and the inlet and between the layer and the outlet). Columns of any other shapes capable of functioning substantially in the same manner may also be used for the same purpose. The column portion in which the adsorbent layer is contained generally has a cylindrical form. The ratio L/D of the cylinder length L to the cylinder diameter D is preferably within the range of 1–5. When L/D is smaller than 1, the blood flows ununiformly through the adsorbent layer and, therefore, the adsorption becomes inefficient. When L/D is larger than 5, the pressure loss becomes so large that hemolysis may occur. When the ratio L/D is within the range of 1–5, blood purification can be performed most efficiently. The column material is, for example, glass, polyethylene, polypropylene, polycarbonate, polystyrene or poly(methyl methacrylate). Among them, polypropylene and polycarbonate, for instance, which can undergo steam sterilization, are particularly preferred. The filter material may be any of physiologically inert and mechanically strong materials, among which polyester and polypropylene are most preferred.

The column with the porous granules packed therein is generally sterilized prior to use, preferably by steam sterilization or γ-ray sterilization.

Figure 3:
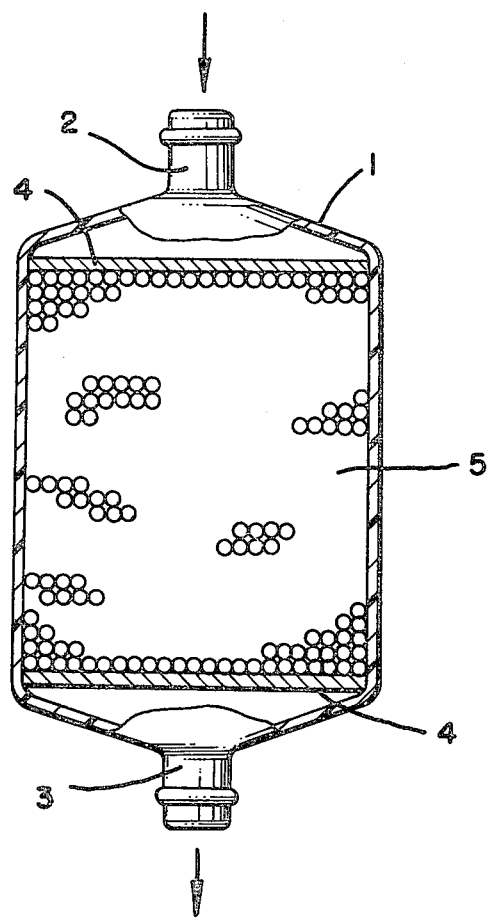
FIG. 3 illustrates, in section, a blood purification device in accordance with the invention, and FIG. 4 schematically shows a mode of blood purification using a blood purification device in accordance with the invention.
Figure 4:
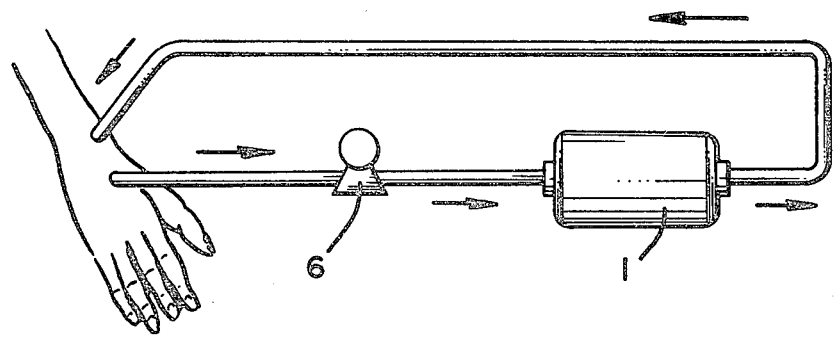

Referring to the drawing, the blood purification device in accordance with the invention is described in more detail. In FIG. 3, an example of the blood purification device is illustrated in section. The main body element 1 has a blood inlet 2 and a blood outlet 3, and contains filters 4 and an adsorbent layer 5. The blood is introduced into the device through 2, the proteins to be removed are adsorbed within the adsorbent layer 5, and the treated blood is taken out through 3. FIG. 4 illustrates the state in which the blood is treated by extracorporeal circulation using the blood purification device in accordance with the invention. The blood derived from the artery is introduced into the blood purification device by means of a pump 6 and, after removal of the target proteins by adsorption, returned to the vein. In this manner, diseases can be treated by removing specific proteins from the blood by adsorption.

The diseases to be treated using the blood purification device include, among others, immune diseases, cancer diseases, familial hypercholesterolemia, hepatic diseases and renal diseases, including systemic lupus erythematosus, chronic rheumatoid arthritis, chronic glomerulonephritis, myasthenia gravis, multiple sclerosis, polymyositis, Bechet's disease, Sjögren's syndrome, scleroderma, eosinophilic granuloma, Heerfordt's syndrome, Wegener's granulomatosis, bronchial asthma, eosinophilic pneumonia, chronic aggressive hepatitis, primary biliary hepatic cirrhosis, ankylosing spondylarthritis, diabetes, polyarteritis, aplastic anemia, autoimmune hemolytic anemia, Flety's syndrome, idiopathic thrombocytopenic purpura and graft rejection.

The blood purification device in accordance with the invention can treat not only the whole blood as it is but also the plasma alone following preliminary separation of the blood into cell components and plasma by means of a selectively permeable membrane or a centrifuge, for instance.

The invention is further illustrated by, but not limited to, the following examples.

EXAMPLE 1 AND COMPARATIVE EXAMPLE 1

A polypropylene column was packed with 50 cc of spherical porous glass granules with 135 mesh polyester filters disposed between the blood inlet and the adsorbent layer and between the blood outlet and the adsorbent layer. The porous glass granules had a surface silanol group concentration of 0.85 $\mu$mole/m$^2$, a mean pore diameter (D) of 450 angstroms, a pore volume of 0.8 cc/g and a granule diameter range of 0.5–1.0 mm, and the ratio of the volume occupied by pores with diameters of 0.8D–1.2D to the whole pore volume of 90 percent (Example 1). For comparison, the same column was packed with 50 cc of crushed porous glass granules CPG-10-350 (Electro Nucleonics; silanol group concentration: 0.67 $\mu$mole/m$^2$; mean pore diameter (D): 380 angstroms; ratio of the volume occupied by pores with diameters of 0.8D–1.2D to the whole pore volume: 86%; granule size: 0.125–0.177 mm) (Comparative Example 1).

The whole blood of rabbits (male, 3.5–4.0 kg) was circulated through each column at a flow rate of about 5 ml/min for 4 hours, and the changes with time in blood cell count and protein concentration of the circulating blood were followed. The percent removal values for albumin and γ-globulin were calculated from the respective peak height ratios as obtained by high performance liquid chromatography [apparatus: Waters model ALC/GPC 244; column: Toyo Soda G-3000 SW (inside diameter 7.5 mm, length 600 mm); eluent: 1/15 M phosphate buffer (containing 0.15 M NaCl, pH 6.0); flow rate: 1.0 ml/min; detection: UV (280 nm)]. The blood cell counting was performed using Toa Medical Electronics' blood cell counter and platelet counter.

TABLE 1

Changes in protein concentration and blood cell count before and after extracorporeal circulation

| | Example 1 | | Comparative Example 1 | |
| --- | --- | --- | --- | --- |
| | Before | After 4 hrs. | Before | After 4 hrs. |
| % Albumin removal | — | 22 | — | 24 |

TABLE 1-continued

Changes in protein concentration and blood cell count before and after extracorporeal circulation

| | Example 1 | | Comparative Example 1 | |
|---|---|---|---|---|
| | Before | After 4 hrs. | Before | After 4 hrs. |
| % γ-Globulin removal | — | 81 | — | 77 |
| Red blood cell count ($\times 10^4/mm^3$) | 643 | 621 | 686 | 575 |
| White blood cell count ($\times 10^3/mm^3$) | 12.5 | 11.8 | 21.1 | 7.1 |
| Platelet count ($\times 10^3/mm^3$) | 413 | 368 | 458 | 87 |

In Comparative Example 1, in which crushed porous granules were packed, the white blood cell count decreased to less than half and the platelet count to one fifth, and thus the influence on blood components was great. On the other hand, in Example 1, in which spherical porous granules were packed, the changes in blood cell count were little and the effect of the invention was evident.

COMPARATIVE EXAMPLE 2

The same experiment as described in Example 1 was conducted using Mizusawa Chemical Industries' porous alumina "Neobead ® MSC-3" after heating for 3 hours (granule diameter: 0.3-0.8 mm; silanol group concentration: about 0 μmole/m$^2$; mean pore diameter: 540 angstroms; pore volume: 0.285 cc/g). After 4 hours of blood circulation, the percent albumin removal was 5% and the percent γ-globulin removal was 0%, and the object of the invention was not attained.

EXAMPLE 2

15 ml of the rabbit blood containing 120 mg of lysozyme (molecular weight 14,600) was circulated in vitro at 37° C. at a flow rate of about 3 ml/min through a polypropylene column (with 180 mesh polyester filters at the inlet and the outlet) packed with 2 g of spherical porous glass granules (surface silanol group concentration: 0.93 μmole/m$^2$; mean pore diameter D: 95 angstroms; volume ratio of 0.8D-1.2D pores: 93%; pore volume: 0.6 cc/g; granule diameter: 0.5-1.0 mm).

The changes with time in lysozyme, albumin and γ-globulin concentrations were followed in the same manner as described in Example 1. The thus-found percentage removal values for each protein are shown below in Table 2. As is clear from the data in table, the removal of lysozyme was almost complete in 3 hours but the concentrations of albumin and γ-globulin were not decreased at all throughout the experiment. These results indicate that, in the blood purification device in accordance with the invention, desired proteins can selectively be removed by adequately selecting the mean pore diameter of the porous granules to be used.

TABLE 2

Removal of proteins from rabbit blood

| Time hours (s) | Lysozyme (M.W. 14,600) | Albumin (M.W. ca 60,000) | γ-Globulin (M.W. ca 160,000) |
|---|---|---|---|
| 1 | 93% | 0% | 0% |
| 2 | 98 | 0 | 0 |
| 3 | 99 | 0 | 0 |

EXAMPLE 3 AND COMPARATIVE EXAMPLE 3

A 30 cc column was packed with spherical porous glass granules having a mean pore diameter (D) of 450 angstroms (silanol group concentration: 0.75 μmole/m$^2$; volume ratio of 0.8D-1.2D pores: 80%; pore volume: 0.60 cc/g; mean granule diameter: 1.0 mm) in the same manner as described in Example 1 (Example 3). For comparison, the same column as above was packed with crushed porous glass granules having a mean pore diameter (D) of 470 angstroms (silanol group concentration: 0.63 μmole/m$^2$; volume ratio of 0.8D-1.2D pores: 83%; pore volume: 0.81 cc/g; mean granule diameter: 1.0 mm) (Comparative Example 3).

About 60 ml of the rabbit whole blood was circulated at 37° C. through each packed column and the possible relationship between the flow rate and the pressure loss was examined.

The results, which are shown in Table 3, indicated that, within the flow rate range of 8.3-17.9 ml/min, the pressure loss as found between the precolumn and postcolumn values was always smaller by about 5 mmHg in the column of Example 3 than in the column of Comparative Example 3. Thus, the superiority of the column of Example 3 was confirmed. In each case, hemolysis was not observed.

TABLE 3

Relationship between the whole blood flow rate and the pressure loss through the column

| | Pressure loss (mmHg) | |
|---|---|---|
| Flow rate (ml/min) | Example 3 | Comparative Example 3 |
| 8.3 | 15 | 20 |
| 11.0 | 20 | 25 |
| 13.0 | 25 | 30 |
| 17.9 | 30 | 35 |

EXAMPLE 4

The same column as used in Example 3 was packed with spherical porous glass granules having a mean pore diameter (D) of 1,020 angstroms (silanol group concentration: 0.47 μmole/m$^2$; volume ratio of 0.8D-1.2D pores: 86%; pore volume: 0.63 cc/g; mean granule diameter: 1.0 mm).

The rabbit whole blood (80 ml) was circulated through the column at 37° C. at a flow rate of 10 ml/min for 3 hours. Most of the cholesterol in the blood exists in the LDL(low-density lipoprotein)-bound form and it is presumed that the percent cholesterol removal is substantially equal to the percent LDL removal. Therefore, the blood cholesterol levels before and after the adsorption procedure were determined by the orthophthalaldehyde method and the percent cholesterol removal, namely the percent LDL removal, was calculated.

The percent cholesterol removal (or percent LDL removal) was 80%, and the total amount of removed cholesterol was 64 mg. The pressure loss due to the column was about 20 mmHg and constant. Hemolysis was not observed at all.

What is claimed is:

1. A method of purifying the blood which comprises contracting the blood with substantially spherical, porous granules made of a material selected from the group consisting of porous glass, porous silica, and silica-alumina and having at least 0.1μ mole/m$^2$ of the silanol group on the surface thereof and thereby removing a protein from the blood by adsorption.

2. A method of purifying the blood as claimed in claim 1, wherein the spherical porous granules have a mean pore diameter of 350–900 angstroms and the protein fraction includes γ-globulin.

3. A method of purifying the blood as claimed in claim 1, wherein the spherical porous granules have a mean pore diameter of 900–1,600 angstroms and the protein fraction includes the low-density lipoprotein.

4. A method of purifying the blood as claimed in claim 1, the majority of the spherical porous granules a diameter within the range of 0.1 mm to 5 mm.

5. A method of purifying the blood as claimed in claim 1, wherein the majority of the spherical porous granules have a diameter within the range of 0.5 mm to 1 mm.

6. A method of purifying the blood as claimed in claim 1, wherein the spherical porous granules have a pore volume within the range of 0.3 cc/g to 2.0 cc/g.

7. A method of purifying the blood as claimed in claim 1, wherein the spherical porous granules have a pore diameter within the range of 20 angstroms to 3,000 angstroms.

8. A method of purifying the blood as claimed in claim 1, wherein the ratio of the volume occupied by pores with diameters within the range of 0.8D–1.2D to the whole pore volume is at least 80%, D being the mean pore diameter.

9. A method of purifying the blood as claimed in claim 1, wherein the spherical porous granules are made of porous glass.

* * * * *

UNITED STATES PATENT AND TRADEMARK OFFICE
CERTIFICATE OF CORRECTION

PATENT NO. : 4,472,303

DATED : September 18, 1984

INVENTOR(S) : Masao Tanihara et al

It is certified that error appears in the above-identified patent and that said Letters Patent is hereby corrected as shown below:

Column 9
In Claim 4, line 2, after "Claim 1," and before "the" insert --wherein--; same line, after "granules" and before "a", insert --have--.

Signed and Sealed this

Nineteenth Day of February 1985

[SEAL]

Attest:

DONALD J. QUIGG

Attesting Officer

Acting Commissioner of Patents and Trademarks